United States Patent [19]

Brackett

[11] Plant 4,418

[45] May 22, 1979

[54] PEACH TREE

[75] Inventor: Leroy W. Brackett, Yakima, Wash.

[73] Assignee: May Nursery Company, Yakima, Wash.

[21] Appl. No.: 886,930

[22] Filed: Mar. 15, 1978

[51] Int. Cl.[2] ..... A01H 5/03
[52] U.S. Cl. ..... Plt./43
[58] Field of Search ..... Plt./43

*Primary Examiner*—Robert E. Bagwill

*Attorney, Agent, or Firm*—Christensen, O'Connor, Johnson & Kindness

[57] ABSTRACT

A new peach tree variety discovered as a sport limb growing on an Early Elberta Freestone Peach Tree. The new variety exhibits excellent winter and spring freeze resistance characteristics and produces fruit under adverse growing conditions that inhibit production by the parent trees and, moreover, fruit that matures some seven to ten days earlier than that of its parent.

5 Drawing Figures

BACKGROUND OF INVENTION

This invention or discovery relates to a new and distinct variety of Early Elberta Freestone peach tree which originated as a sport limb on a parent tree of that variety discovered in an orchard at Yakima, Wash. and that has been asexually reproduced by applicant.

DESCRIPTION OF ILLUSTRATIONS

FIG. 1 is a photograph of a young tree of the new variety.

FIG. 2 is a photograph of a spray of branches bearing blossoms.

FIG. 3 is a photograph of the original tree exhibiting the sport limb bearing fruit, such limb being located on the near side and slightly to the right of center, i.e., that on which most of the fruit appears to be concentrated (after a severe winter).

FIG. 4 is a closeup photograph of the sport limb bearing ripened fruit.

FIG. 5 is a photograph of a peach of the new variety shown in the whole and one shown split in half with the stone removed.

This new variety is characterized in part in that the tree structure, including the trunk, limbs, bark, spurs, leaves and other characteristics are generally the same as the parent Early Elberta Freestone tree. However, its leaves are deeper green, with an estimated 15% to 20% more chlorophyll than its parent, and unlike the original or parent tree, the new variety has proved capable of providing a full crop of fruit under conditions of winter freeze that precluded fruiting of the parent tree. The fruit of this new variety matures some seven to ten days earlier than that of its parent under the same growing conditions. Moreover, its trees are more upright in growth habit and with smaller scaffolding than the parent trees.

The new variety has been reproduced through successive generations, accompanied by observations of each generation with respect to fruiting characteristics and other properties. The new variety proves to be stable in all of its identifying characteristics, including its ability to withstand adverse winter or spring freeze or frosting conditions, which killed the buds of the standard Early Elberta Freestone trees in the same vicinity.

The fruit of this new mutation is of medium size, firm, fairly round, with a slight flattening on the limb side of the fruit. The apex is blunt or unpointed. Of the true freestone type, the flesh is smooth, juicy and firm with very litle fiber content. The flavor is excellent. Its firmness and keeping properties make the fruit desirable for shipping and processing.

Externally the fruit is colored similarly to Early Elberta, namely a red blush (SR 4/12 on Nickerson color fan chart) with slight mottling effect over the yellow background (YR 8/8 on Nickerson color fan chart). There is slightly more intensity to red blush than is exhibited on the parent Early Elberta fruit.

I claim:

1. A new and distinct variety of Early Elberta Freestone peach tree characterized by its winter hardiness, by its more upright growth habit with smaller scaffolding, by its more deeply green leaves, by its fruit that is similar to that of its parent but that matures some seven to ten days earlier, and by its ability to produce a full crop of fruit despite adverse winter or spring freeze conditions fatal to crop production in the Early Elberta Freestone peach trees growing in the same vicinity, as illustrated and described.

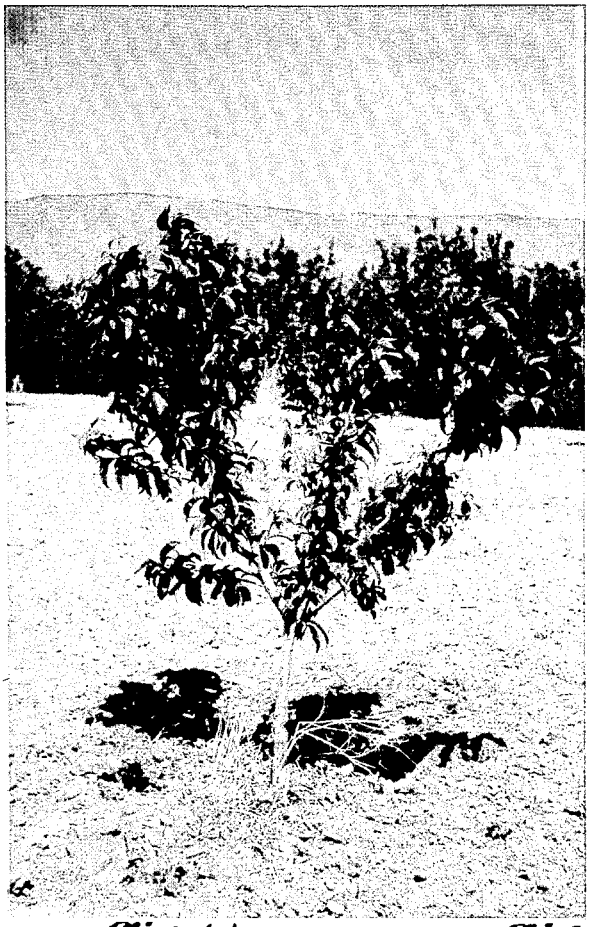
Fig. 1.
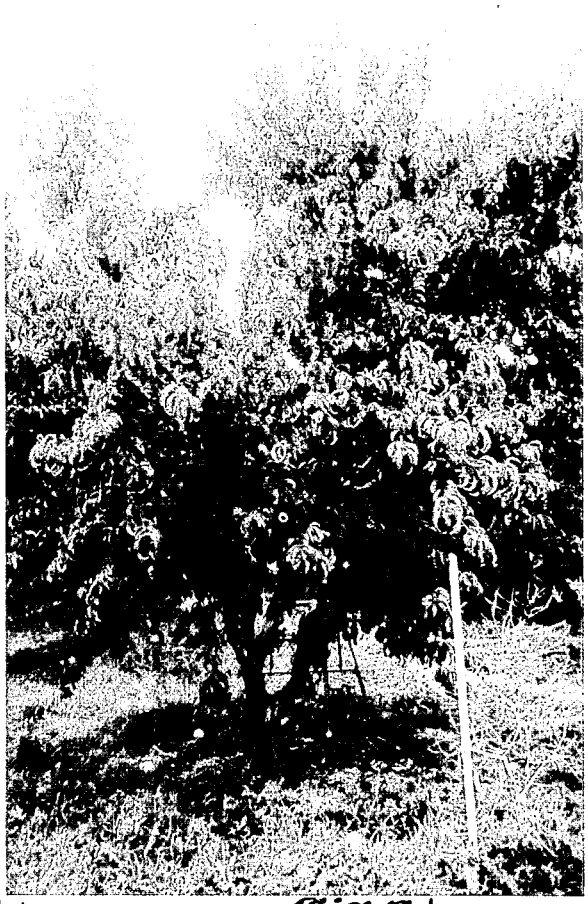
Fig. 2.
Fig. 3
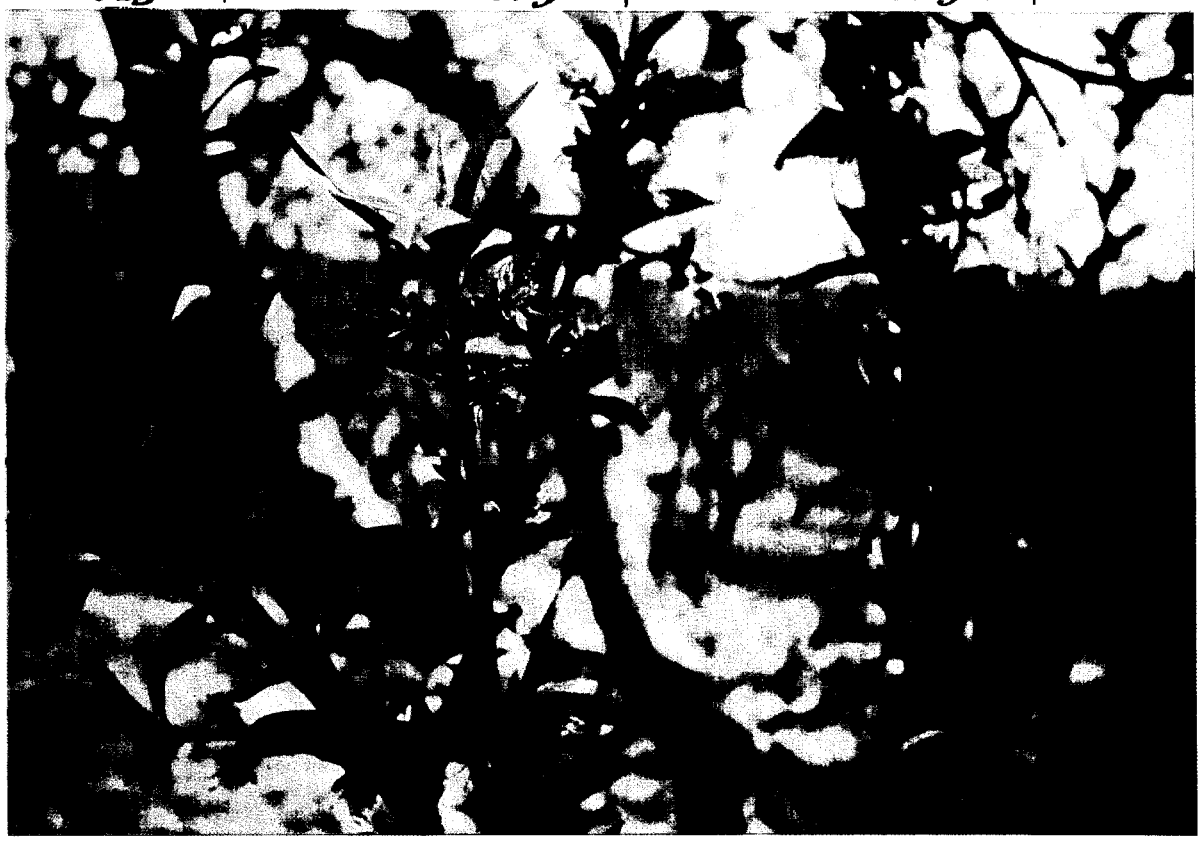

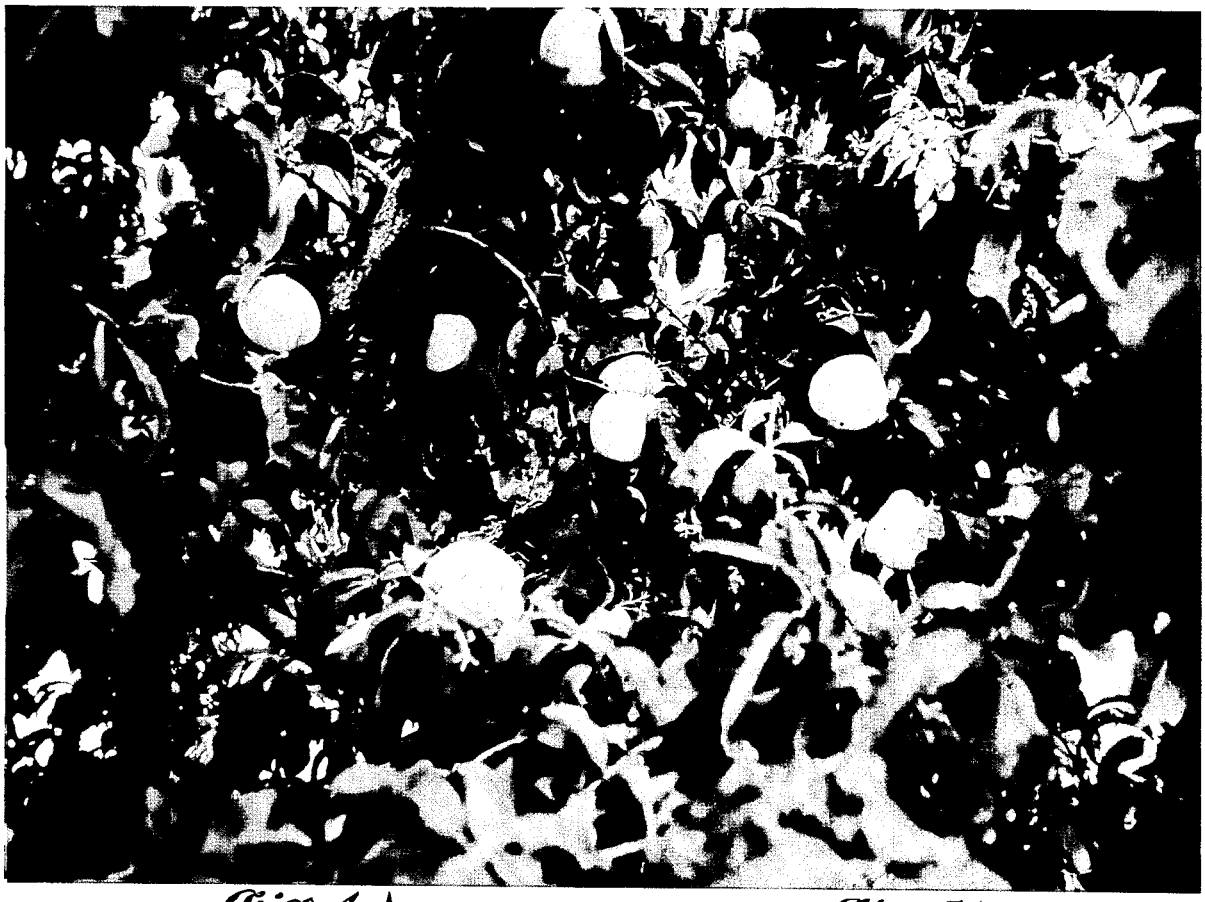
Fig. 4. ↑
Fig. 5. ↓
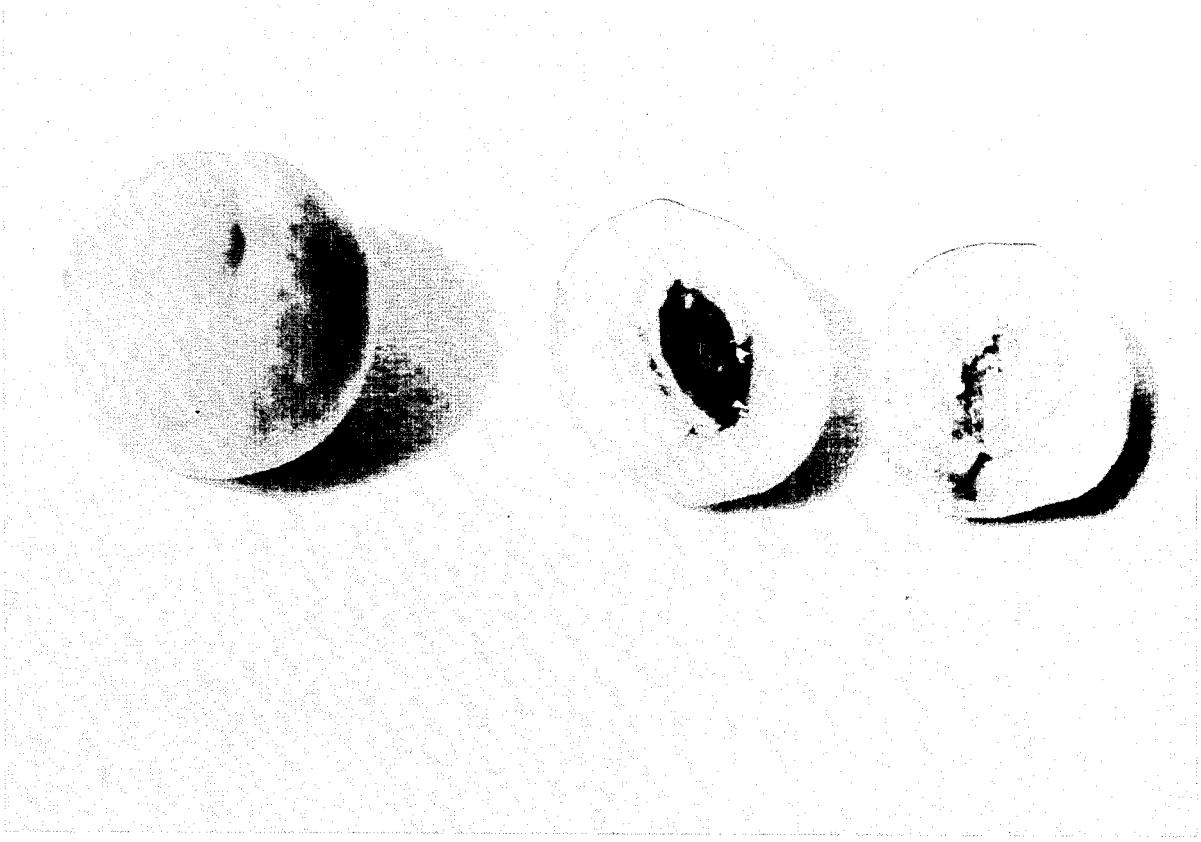

* * * * *